US 6,728,655 B2

United States Patent
Stark

(10) Patent No.: US 6,728,655 B2
(45) Date of Patent: Apr. 27, 2004

(54) CUSTOMIZABLE AND EXTENDABLE DATA PROCESSING ARCHITECTURE FOR A DATA ACQUISITION INSTRUMENT

(75) Inventor: Donald Wilson Stark, Santa Rosa, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 95 days.

(21) Appl. No.: 09/944,992

(22) Filed: Aug. 31, 2001

(65) Prior Publication Data

US 2003/0125898 A1 Jul. 3, 2003

(51) Int. Cl.[7] .............................................. G06F 19/00
(52) U.S. Cl. ......................................... 702/123; 700/89
(58) Field of Search ........................... 702/66, 123, 62, 702/119, 68, 76, 20, 18; 324/638, 646; 345/440, 788, 173, 765; 700/83–84, 86–87, 89

(56) References Cited

U.S. PATENT DOCUMENTS

| 5,790,977 A | * | 8/1998 | Ezekiel | 702/122 |
| 2002/0188428 A1 | | 12/2002 | Faust | 702/188 |

OTHER PUBLICATIONS

*Agilent 8719D, 8720D, and 8722D Microwave Vector Network Analyzers* brochure, available as part number 5966–4007E, copyright 1998,2000, from Agilent Technologies, Inc.

* cited by examiner

Primary Examiner—Marc S. Hoff
Assistant Examiner—Mary Catherine Baran

(57) ABSTRACT

An electronic instrument includes instrument hardware, core software, and the ability to support custom data processing libraries, separate from the core software. The instrument hardware acquires unprocessed measured data. The core software includes standard measurement objects and standard algorithms. The standard measurement objects produce analysis results of the unprocessed measured data. The standard algorithms are used by the standard measurement objects to aid in production of analysis results of the unprocessed measured data. Custom libraries as supported by the core software include custom measurement objects and custom algorithms. The custom measurement objects produce analysis results of the unprocessed measured data. The custom algorithms are used by the custom measurement objects to aid in production of analysis results of the unprocessed measured data. The custom measurement objects also are capable of using the standard algorithms to aid in production of analysis results of the unprocessed measured data.

22 Claims, 10 Drawing Sheets

CUSTOMIZABLE AND EXTENDABLE DATA PROCESSING ARCHITECTURE FOR A DATA ACQUISITION INSTRUMENT

RELATED APPLICATION

The present invention concerns subject matter related to a co-pending patent application Ser. No. 09/796,159, by Dennis John McCarthy and Donald Wilson Stark entitled: SORTING DATA BASED ON DATA ATTRIBUTES FOR DISPLAY IN MULTIPLE DISPLAY WINDOWS and filed on Feb. 28, 2001 and to a co-pending patent application Ser. No. 09/809,702, by Donald Wilson Stark entitled: DATA ACQUISITION INSTRUMENT ARCHITECTURE WITH FLEXIBLE DATA ACQUISITION, PROCESSING AND DISPLAY and filed on Mar. 14, 2001.

BACKGROUND

The present invention concerns data processing and pertains particularly to a customizable and extendable data processing architecture for a data acquisition instrument Electronic instruments such as network analyzers and spectrum analyzers often allow data acquisition over many channels and include a display capable of displaying one or more traces. For example, Model Number 8719D microwave vector network analyzers are available from Agilent Technologies, Inc., having a business address of 395 Page Mill Road, P.O. Box #10395, Palo Alto, Calif. 94306. An 8719D microwave vector network analyzer has a four parameter display that can display all four S-parameters simultaneously. Any combination of reflection and transmission parameters can be displayed, with magnitude, phase, group delay, Smith chart, polar, standing wave ratio (SWR), or time-domain formats. Results may viewed in overlay or split-screen format on a liquid crystal display (LCD) color display with one, two or four graticules. See, for example, *Agilent 8719D, 8720D, and 8722D Microwave Vector Network Analyzers* brochure, available as part number 5966-4007E, copyright 1998,2000, from Agilent Technologies, Inc.

Architecture for prior art network analyzers tend to allow limited post-processing options. For example, previous network analyzers have a fixed number of measurements and algorithms that can be performed. Software in network analyzers are typically limited to an S-Parameter, arbitrary receiver ratio, or unratioed receiver data. Additional results typically can only be obtained by writing a program the runs on a computing system external to the network analyzer. An external computer running such a program may have the capability to query for S-Parameter, arbitrary ratio, or raw receiver data and externally performs more sophisticated computations such as a K-Factor computation. The drawback with using an external computer is that this incurs the overhead of transporting data via some input/output (I/O) mechanism to the external computer. Also, since the desired final computed result exists on the external computer, the standard network analyzer software analysis features such as marker or limit line testing cannot be applied for further analysis (unless they are rewritten in the external program). Also, the network analyzer's data display cannot be used. Some of the utility of the network analyzer's software has been traded for the ability to perform a more sophisticated data computation than is offered by the standard network analyzer software.

SUMMARY OF THE INVENTION

In accordance with the preferred embodiment of the present invention, an electronic instrument includes instrument hardware, core software, and the ability to support custom data processing libraries, separate from the core software. The instrument hardware acquires unprocessed measured data. The core software includes standard measurement objects and standard algorithms. The standard measurement objects produce analysis results of the unprocessed measured data. The standard algorithms are used by the standard measurement objects to aid in production of analysis results of the unprocessed measured data. Custom libraries as supported by the core software include custom measurement objects and custom algorithms. The custom measurement objects produce analysis results of the unprocessed measured data. The custom algorithms are used by the custom measurement objects to aid in production of analysis results of the unprocessed measured data. The custom measurement objects also are capable of using the standard algorithms to aid in production of analysis results of the unprocessed measured data.

DESCRIPTION OF THE PREFERRED EMBODIMENT

Figure 1:
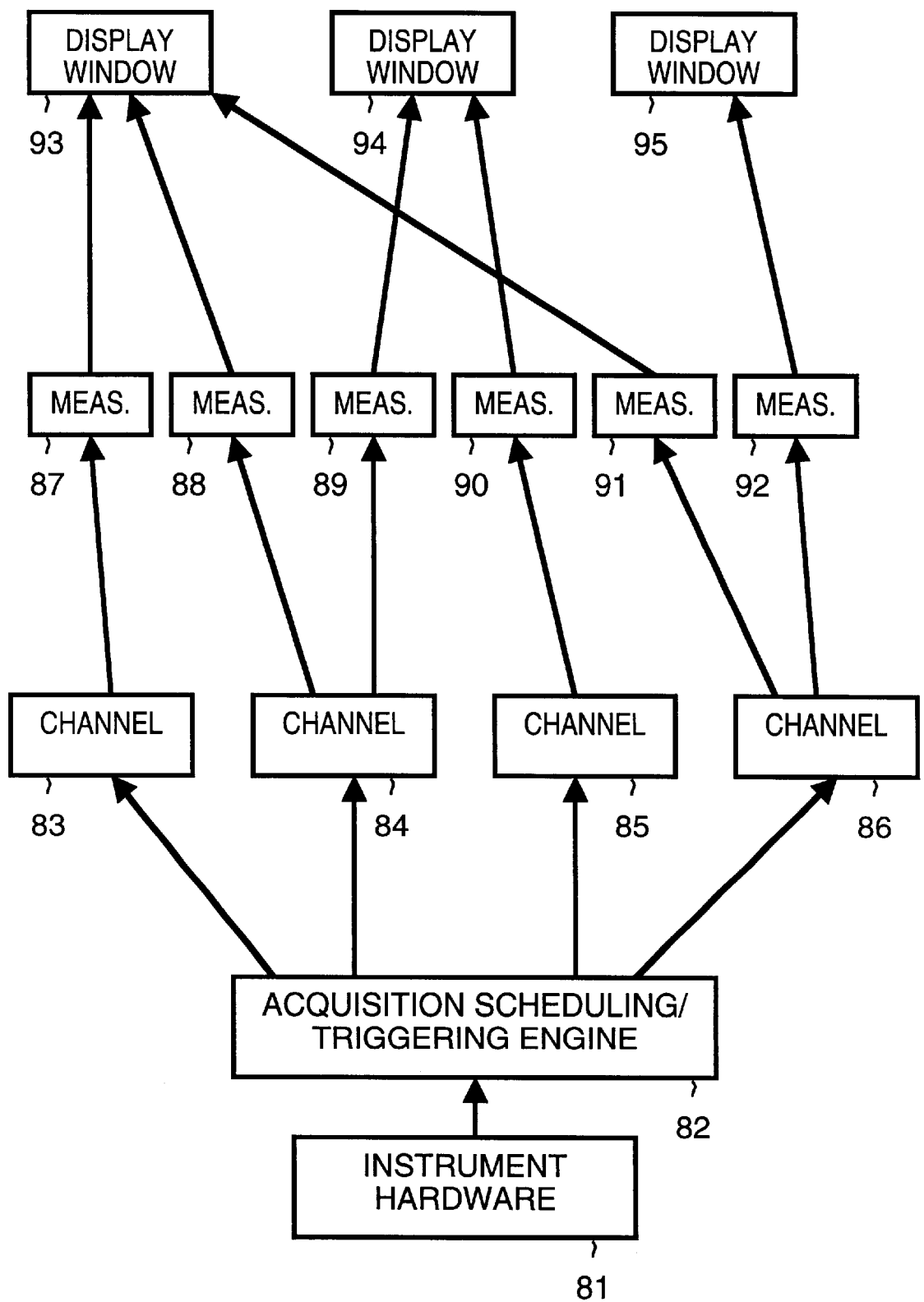
FIG. 1 is a diagram that illustrates use of a three stage data process for operation of a data acquisition instrument architecture, in accordance with a preferred embodiment of the present invention.

FIG. 1 illustrates use of a three stage data process for operation of a data acquisition instrument architecture. The three stages are acquisition, data post-processing, and data display An acquisition scheduling/triggering engine 82 employs up to an arbitrary number N (limited by device memory) dynamically allocated instances of 'virtual' sub-instruments to simultaneously co-exist and share an instrument hardware 81. For example, instrument hardware 81 is the hardware for a network analyzer. Alternatively, instrument hardware 81 can be instrument hardware for another type of instrument. Since instrument hardware 81 is a limited and expensive resource, acquisition scheduling/triggering engine 82 schedules the sub-instruments use the single hardware resource in a time-shared fashion.

Each sub-instrument acts as a channel object. In FIG. 1, sub-instruments are represented by a channel object 83, a channel object 84, a channel object 85 and a channel object 86. The number of channel objects dynamically created by the software depends on user demands. A user-configurable scheme allows for arming and triggering the channel objects in a data acquisition sequence. This scheme allows an instrument user to simultaneously set up and use an arbitrary number (N) different channel data requests that the system can then execute on instrument hardware 81. The result of these executions are one or more data buffers corresponding to the channel objects. The N channel scheme results in maximum flexibility for the instrument user in the area of data acquisition compared to other schemes that limit the number of acquisition channels.

In data post processing, once the channel data buffers are acquired by the hardware during the acquisition phase, the channel objects are made available to an arbitrary number (N) of measurement objects. A measurement object is a digital computer bound data processing chain not requiring analog hardware. In FIG. 1, the measurement objects are represented by a measurement object 87, a measurement object 88, a measurement object 89, a measurement object 90, a measurement object 91 and a measurement object 92. The number of dynamically created measurement objects depends on the user's requirements, and is independent of the number of channel objects. Thus raw channel data buffers can be processed by N different measurement objects to produce different results, depending on the data processing specified to be performed by each individual measurement object. The benefit here is that the raw channel data was only acquired once from instrument hardware 81, but can be processed multiple (up to N) times to provide the user with multiple near-simultaneous analyses of the same original data, resulting in quicker overall data analysis compared to a system that acquires data more than once to accomplish the same task.

In data display, once each of the N measurement objects has produced results, those results can be displayed in a display window. The measurement objects can be arbitrarily organized and combined into display windows. This is illustrated in FIG. 1 by a display window 93, a display window 94 and a display window 95. Thus a user has maximum flexibility to configure how measured and post-processed data appears on the instrument display.

The flexibility of the connections between the three stages is achieved by using an event driven update mechanism. This mechanism is what allows an arbitrary number of data clients to "subscribe" to events describing changing data. For example, in this system a measurement object subscribes to a channel object so that the measurement object will be notified when the data that the measurement object is interested in is changed/updated during-the hardware data acquisition process. The same event/subscription mechanism is used between the display and data processing layers as well.

Because of the dynamic nature of how data is measured, processed, and displayed in this architecture, it is necessary to provide names so that portions of the acquisition and processing chain can be addressed and modified (particularly from remote programming environments). Thus a user is allowed to provide a name, or the software automatically generates a descriptive name based on attributes of the data processing chain.

Data is provided by acquisition scheduling/triggering engine 82 via a client/server mechanism where the acquisition scheduling/triggering engine 82 is the server, and clients are an arbitrary number (N) of abstractly defined (in classic object-oriented sense) pieces of software (e.g., channel objects) that want data from the instrument hardware 81.

Acquisition scheduling/triggering engine 82 is responsible for scheduling requests for instrument hardware 81 data made by the clients of acquisition scheduling/triggering engine 82. Acquisition scheduling/triggering engine 82 time-shares instrument hardware 81 among its clients that want data, since in the preferred embodiment, instrument hardware 81 can only do one thing at a time. Acquisition scheduling/triggering engine 82 supports an arbitrary number of clients (limited by available memory). Acquisition scheduling/triggering engine 82 is also responsible for translating high level client requests for data into a command queue (or command list) which is used to generate actual hardware control signals and data digitization operations. The triggering portion of the generated commands lists changes depending on past and present client requests, and trigger signal inputs.

Most operations of acquisition scheduling/triggering engine 82 execute asynchronously with respect to clients of acquisition scheduling/triggering engine 82. This is necessary to allow acquisition scheduling/triggering engine 82 to respond to requests from instrument hardware 81. Asynchronous execution is achieved by providing acquisition scheduling/triggering engine 82 with a thread of execution, and a message queue from which to process instructions and arguments to those instructions. This thread also allows clients of acquisition scheduling/triggering engine 82 to operate asynchronously from acquisition scheduling/triggering engine 82. This is convenient since given the timesharing and triggering responsibilities of the acquisition scheduling/triggering engine 82, acquisition scheduling/triggering engine 82, clients could otherwise block for long and/or undetermined amounts of time while interacting with acquisition scheduling/triggering engine 82. Acquisition scheduling/triggering engine 82 includes a state machine, which executes given inputs from clients (from "above") and instrument hardware 81 (from "below").

Acquisition scheduling/triggering engine 82 allows the clients to take a group of related hardware measurement objects in sequence (without scheduling another client in between). This is referred to as an acquisition group. Acquisition scheduling/triggering engine 82 also provides support for multiple triggering modes as applied to the clients, including point trigger, channel object, or global. Global trigger mode means that a received trigger signal input applies to all clients. Channel object trigger mode means that a received trigger signal input applies to the "current" client. Point trigger mode implies channel object trigger mode, and means that a received trigger signal input applies to the next data point only. State machine logic within acquisition scheduling/triggering engine 82 can handle changing between these triggering modes as it applies to its clients and instrument hardware 81 in their respective current states.

Acquisition scheduling/triggering engine 82's ability to handle an arbitrary number of abstractly defined clients allows it to support the concept of a virtual hardware instrument. Basically this means that anyone can build a client to use instrument hardware 81 to take data as though the client were the only client.

Channel objects are a type of client of acquisition scheduling/triggering engine 82. Channel objects contain a high level description of desired measurement objects, such as frequency range, power level, IF bandwidth, number of points to sweep, which receivers to measure, etc. that is compatible with acquisition scheduling/triggering engine 82. The channel objects use acquisition scheduling/triggering engine 82 to do the work of actually getting the data from instrument hardware 81 that fits a given description.

Table 1 below sets out an overview of the basic sequence that acquisition scheduling/triggering engine 82 follows:

TABLE 1

System Startup - initialize hardware. Go to IDLE state.
IDLE state:

1) Check to see if hardware needs calibration. If so, calibrate.
2) Check to see if acquisition scheduling/triggering engine 82 is in the process of taking data for a particular client. If there is more data (additional sweeps) to take for this client, build and load and run a command list for that client, then proceed to either SWEEPING state or SWEEPING_NOT_TRIGGERED state depending on triggering setup.
3) If there is no client currently being serviced: Evaluate the client list to see whether there is a client that needs to take data. If so, (based on triggering mode and some client state), begin that process of taking data (prepare a command list consistent with the client's request) and change to either the SWEEPING state or SWEEPING_NOT_TRIGGERED state. Note that evaluating this client list is an optimization of the timeshared hardware usage. Clients that are ready to run are scheduled to run. Clients that are not ready are passed over until they are.

SWEEPING state:

1) As data is taken by instrument hardware 81, return that data to the current client. Since these clients are arbitrary and dynamic in nature a memory buffering scheme has been implemented to maximize data throughput without delivering data to compile-time fixed memory locations. This scheme maximizes overall data throughput whether there is 1, 2, or N clients currently using acquisition scheduling/triggering engine 82.
2) If the sweep is aborted for any reason (hardware errors, or client interruption), return to IDLE state.
3) When the sweep completes, notify client of this fact, and return to IDLE state.

SWEEPING_NOT_TRIGGERED state:

1) Wait for an external (pos. or neg. rear panel) trigger signal input, or an internally generated signal, such as a user pressing a button. When it arrives go to SWEEPING state.
2) If the signal does not arrive, but instead the sweep is aborted, return to IDLE state.

All states:

During the IDLE, SWEEPING, and SWEEPING_NOT_TRIGGERED states, acquisition scheduling/triggering engine 82 must accommodate client requests such as adding and removing clients, and changing the trigger mode and trigger signal. Depending on the state, different actions are taken which may include aborting current sweep operations, reordering the client list.

Figure 2:
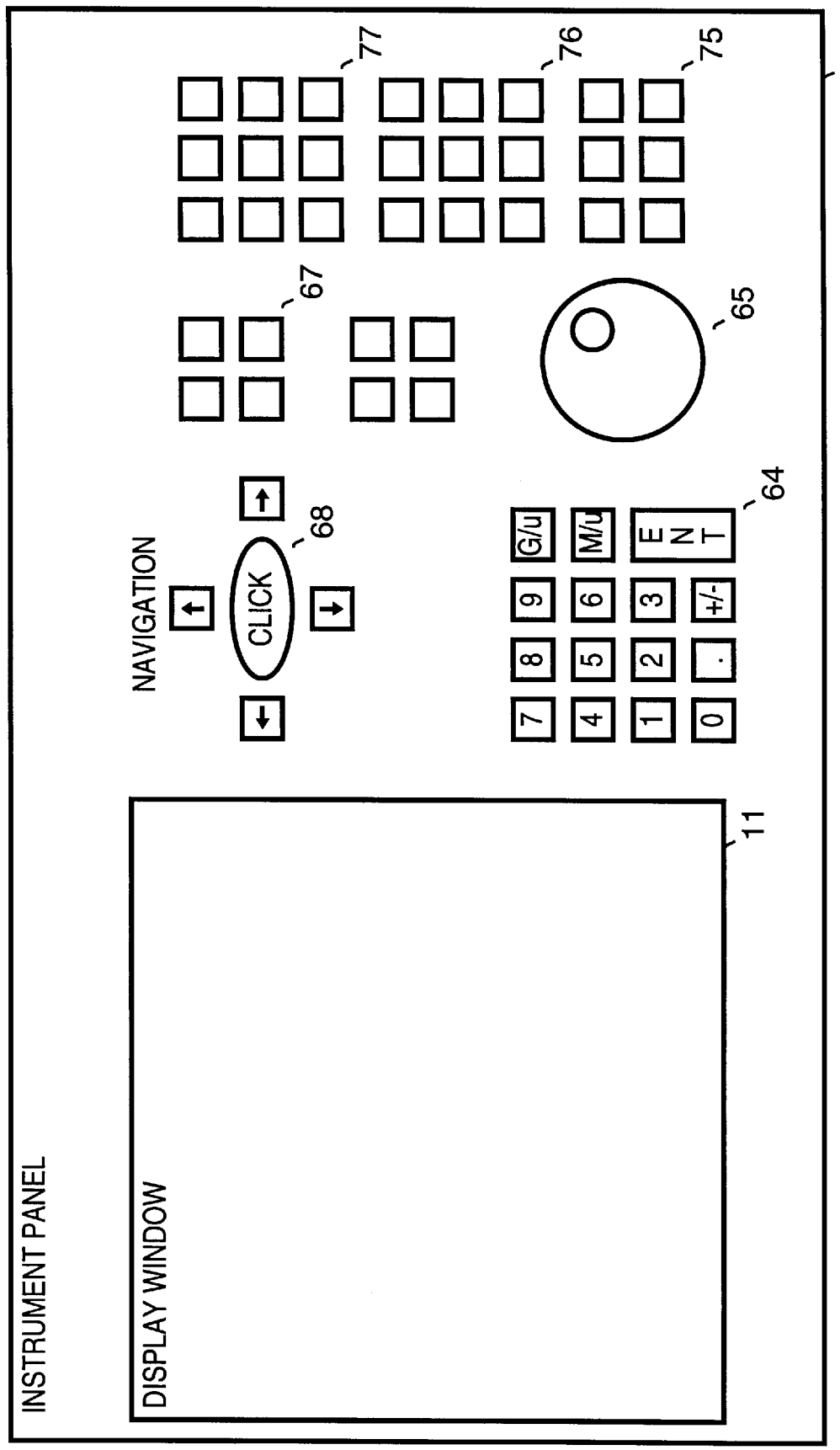
FIG. 2 is a simplified diagram of an instrument panel of an electronic instrument.

FIG. 2 is a simplified diagram of an instrument panel 60 of an electronic instrument. Instrument panel 60 includes an LCD display 11. LCD display 11 is capable of displaying multiple display windows. Instrument panel 60 also includes a navigation tool 68 consisting of hard keys. Navigation tool 68 can be utilized by a user as a point and select interface.

Instrument panel 60 additionally includes a numeric keypad 64 and a knob 65. Display hard keys 67 include a "Trace" key, a "Window" key, a "Measure/Setups" key and an "Arrange windows" key. Control hard keys 66 include an "OK" key, a "help" key, a "Cancel" key and a "Menu/Dialog" key.

Channel object setup hard keys 77 include a "Start/Center" key, a "Stop/'Span" key, a "Power" key, a "Sweep Setup" key, a "channel object" key, a "Sweep Type" key, a "Trigger" key, an "Average" key and a "Calibrate" key.

Trace setup hard keys 76 include a "Measure" key, a "Format" key, a "Scale" key, a "Marker" key, a "Marker Table" key, a "Limit Table" key, a "Marker Search" key, a "Marker Function" key and a "Math/Memory" key.

Utility keys 75 include a "Save" key, a "Maximize" key, a "Preset" key, a "Recall" key, a "Print' key and a "Macro" key.

Table 2 below gives an example of four measurement objects defined by a user for display on display 11.

TABLE 2

|  | Axis Format | Frequency Range | Measurement Object Path |
|---|---|---|---|
| Trace #1 - S11 (Trace 17) | Circular | 10–500 MHz | Reflection |
| Trace #2 - S21 (Trace 15) | Rectangular | 10–500 MHz | Transmission |
| Trace #3 - S21 (Trace 14) | Rectangular | 10–1000 MHz | Transmission |
| Trace #4 - S22 (Trace 13) | Rectangular | 10–500 MHz | Reflection |

The user can select a number of windows to be used to display the traces. Then the traces are distributed into a number of groups equal to the number of windows selected. Those traces that are most similar are grouped together. A set of attributes is used to determine which measurement objects are the most similar. When assigning similar traces to groups, some attributes are considered to be more important than others. When sorting is finished, all of the traces in a group are displayed together in one window.

Figure 3:
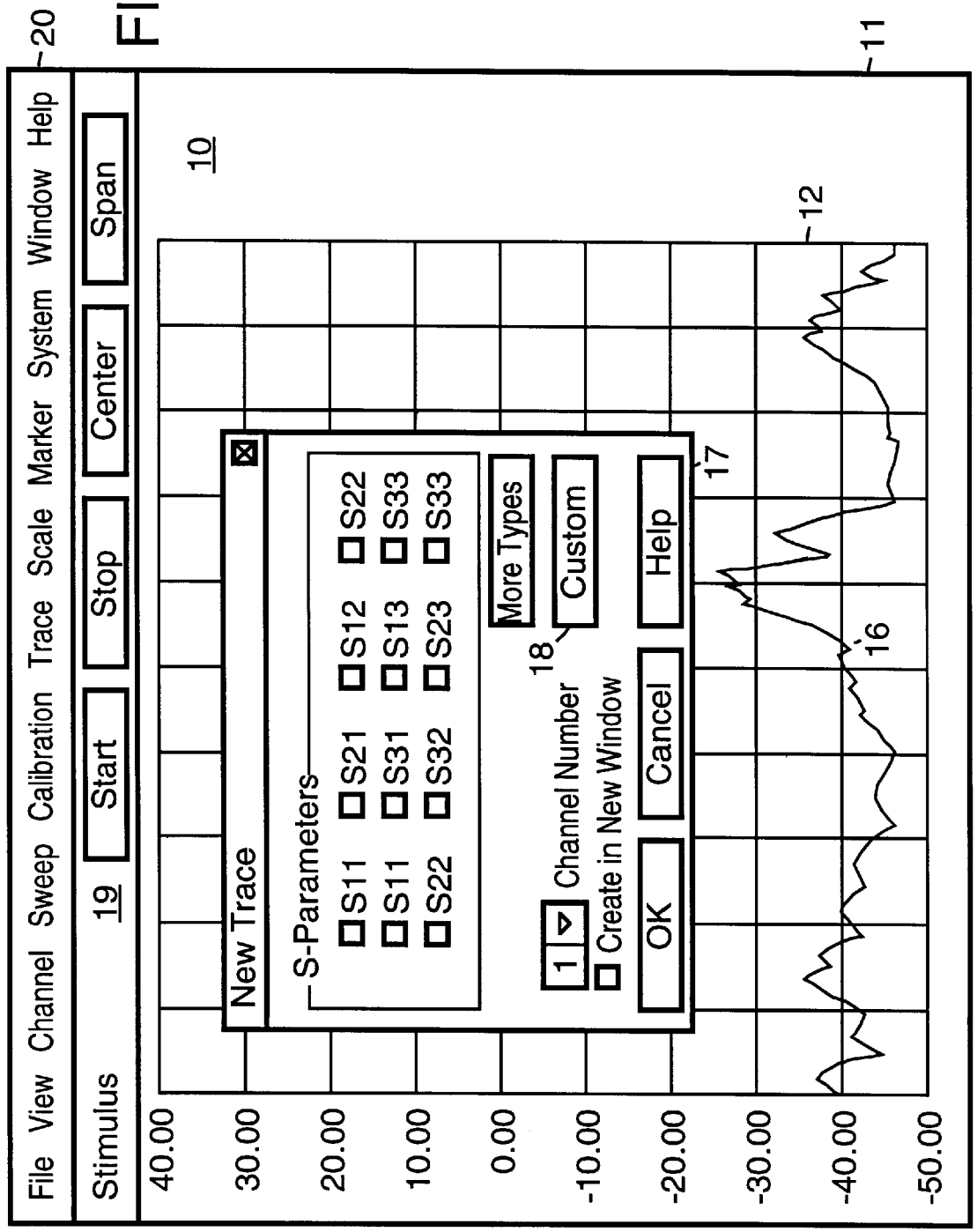
FIG. 3 shows a display window including a dialog box from which custom measurements may be accessed in accordance with a preferred embodiment of the present invention.

In FIG. 3, a display 11 shows a trace 16 displayed in a single window 10. Various interface buttons are displayed on a toolbar 19. Trace 16 is shown relative to a rectangular graticule 12. A dialog box 17 from which custom measurements may be accessed is also shown. Dialog box 17 is a new trace dialog box that a user obtains by choosing Trace = New Trace off menu 20 at the top of display 11. A custom button 18 can be used by a user to interface with custom measurements.

Figure 4:
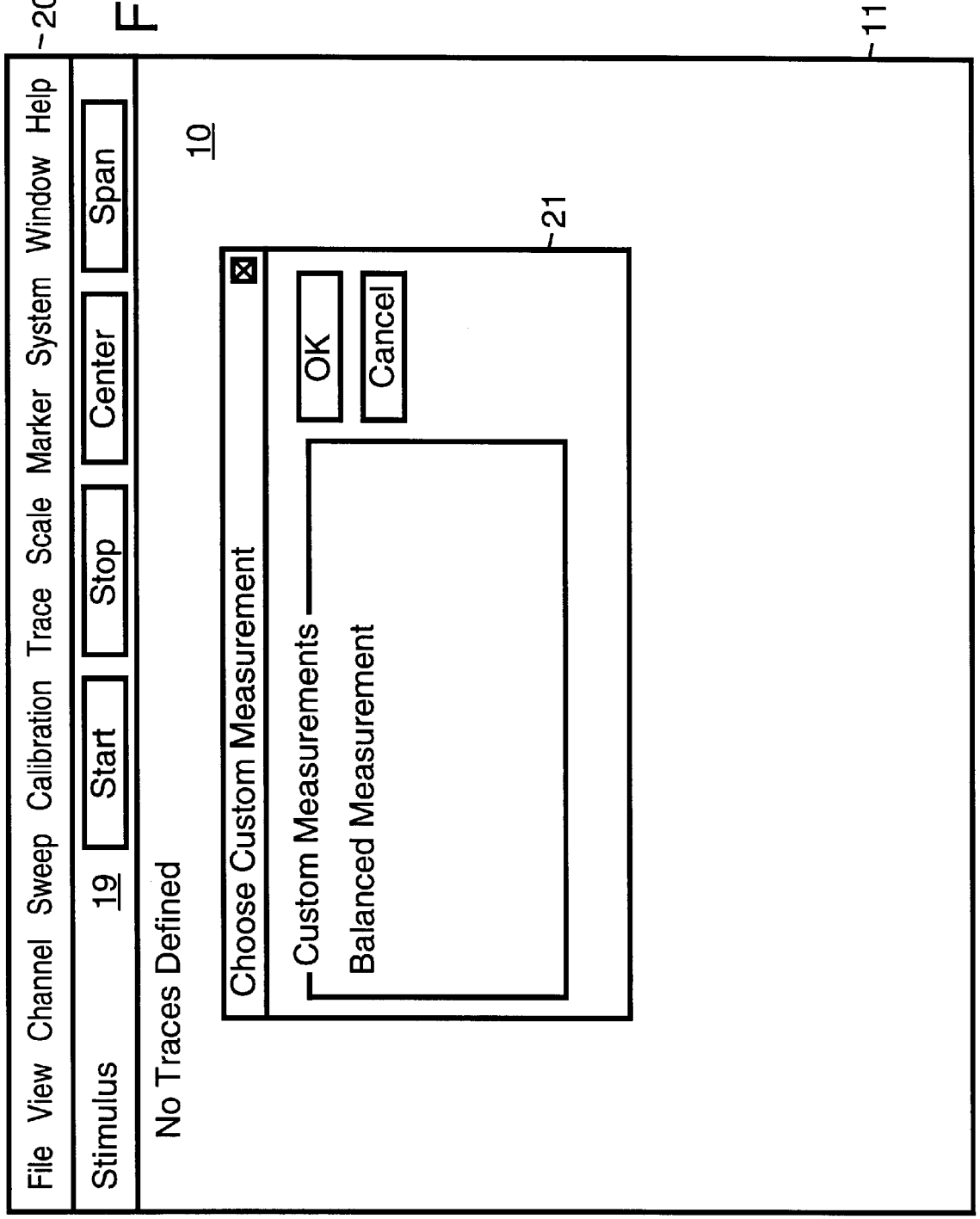
FIG. 4 shows a display window including a dialog box that lists installed custom measurements available to a user in accordance with a preferred embodiment of the present invention.

When a user selects custom button 18, a dialog box 21 appears, as shown in FIG. 4. Dialog box 21 presents the user with a list of installed custom measurements to choose from when creating a new (custom) measurement. In FIG. 4, dialog box shows a "Balanced Measurement" entry (another term for mixed mode) that is an installed custom measurement choice.

Figure 5:
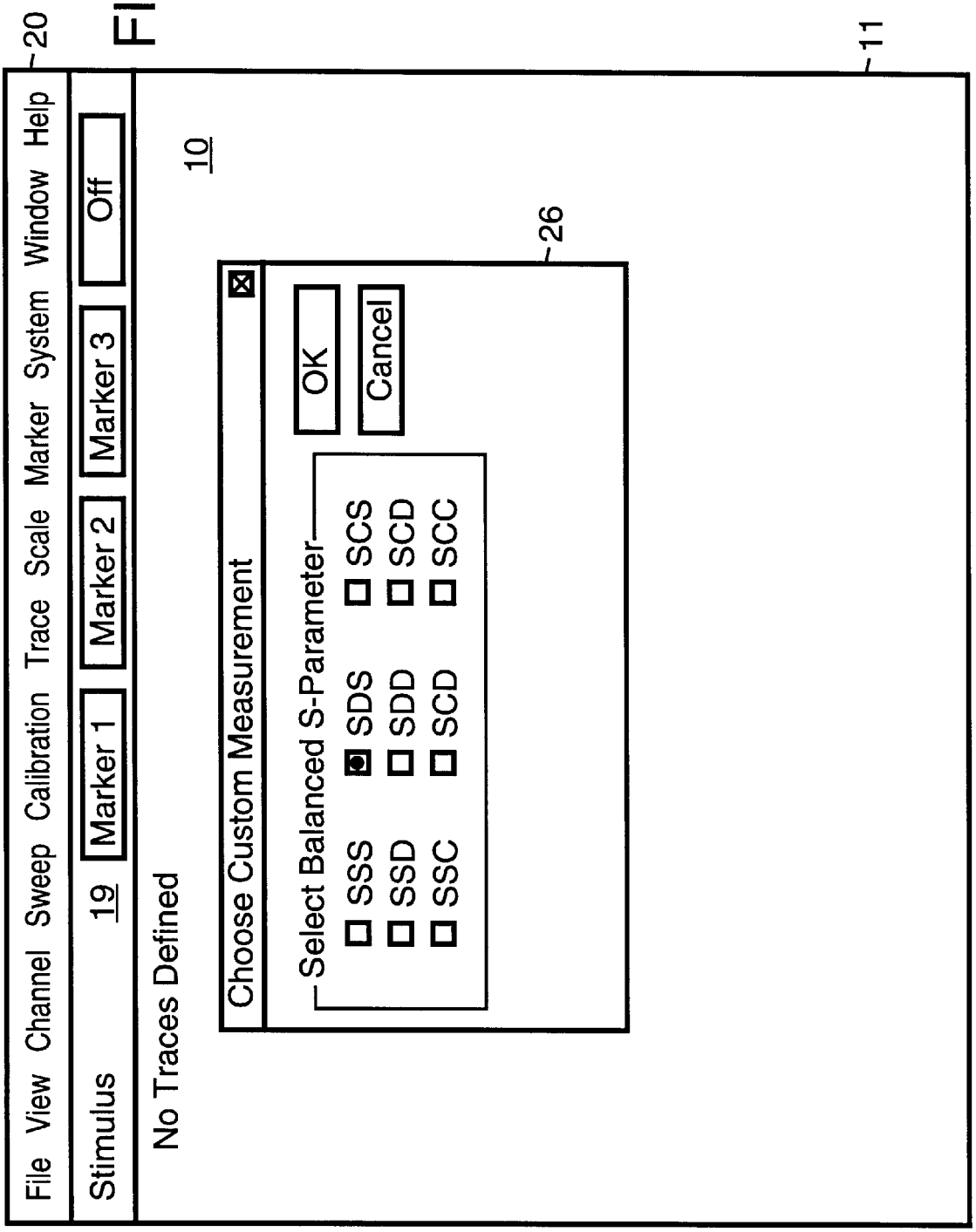
FIG. 5 shows a display window including a dialog box that is available to a user as an interface for a custom measurement in accordance with a preferred embodiment of the present invention.

When a user selects to create a balanced S-parameter, a dialog box 26 is displayed, as shown in FIG. 5. Dialog box 26 allows a user to select one of nine different possible balanced S parameters. Dialog box 26 is a graphic user interface provided by the custom measurement.

Figure 6:
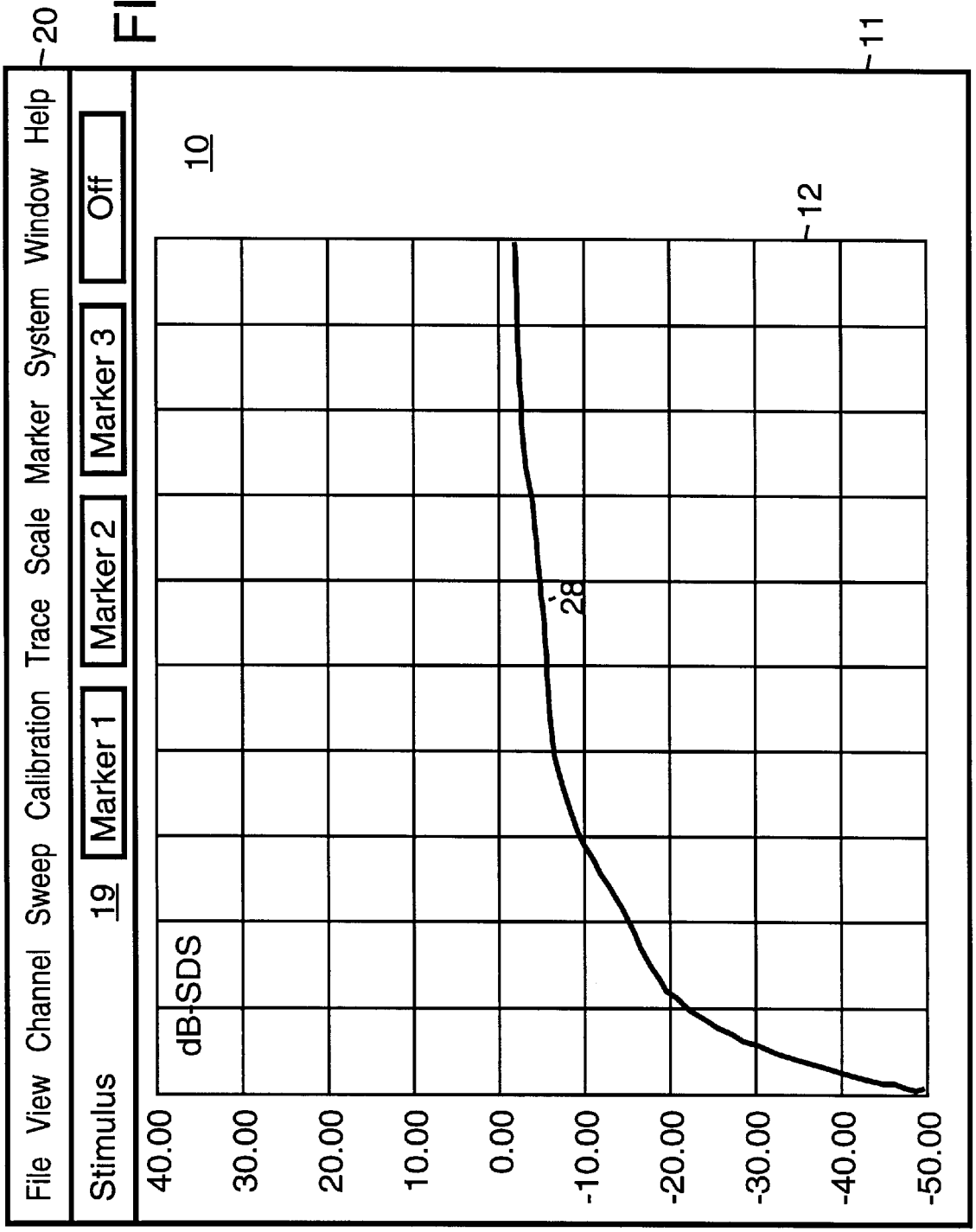
FIG. 6 shows a display window showing the result of performing a custom measurement in accordance with a preferred embodiment of the present invention.

As seen in FIG. 5, a user has selected the "SDS" Balanced measurement. FIG. 6 shows a trace 28 for the SDS balanced measurement as placed upon graticule 12. The annotation "dB-SDS" is displayed. Standard formatting, markers, and limit lines all work with the custom data processing.

Figure 7:
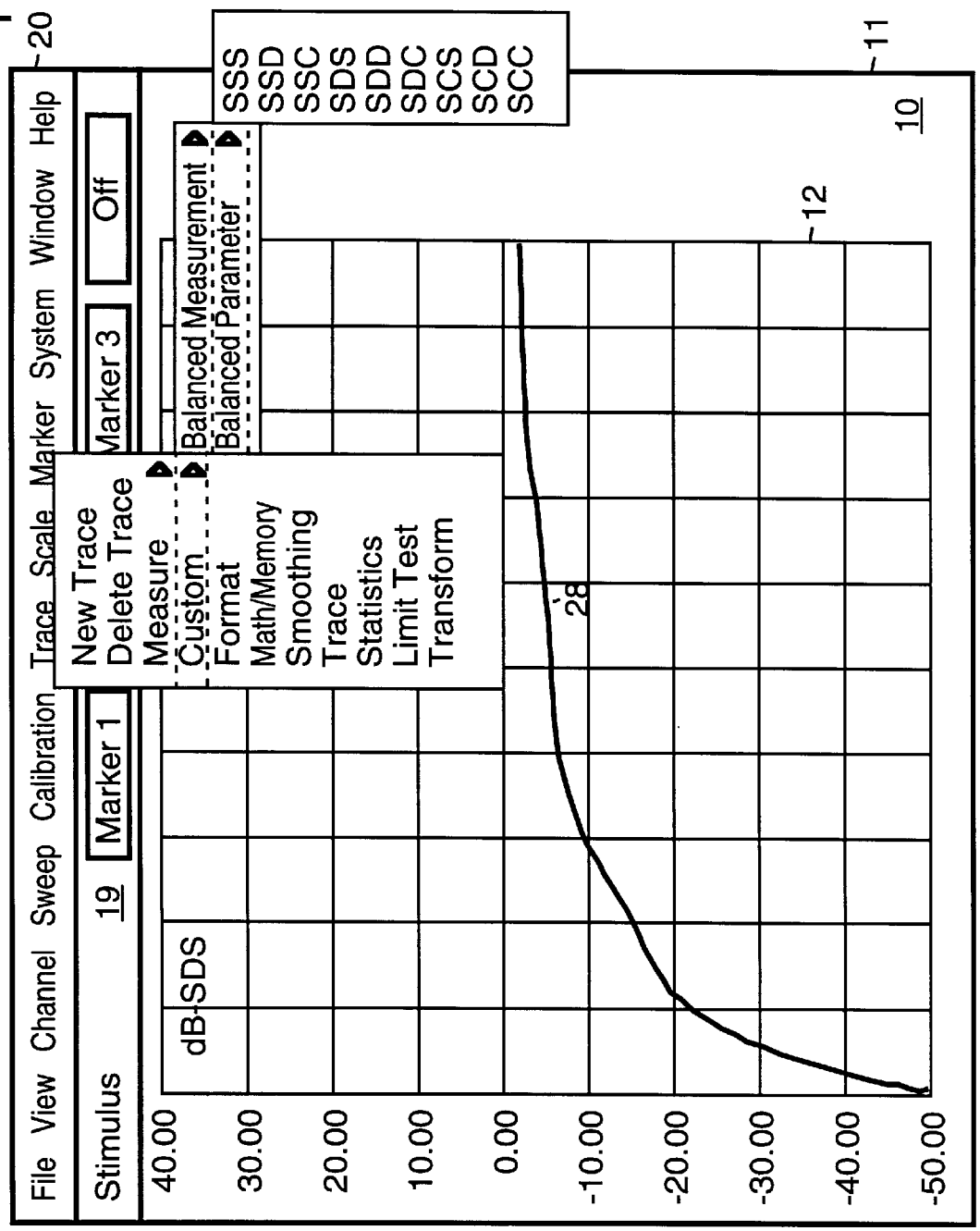
FIG. 7 shows a display window including a menu from which custom measurements may be accessed in accordance with a preferred embodiment of the present invention.

Custom measurements may also be selected using the trace menu from menus 20 displayed at the top of display 11. For example, FIG. 7 shows a user selecting Trace|Custom|Balanced Parameter in order to list the S parameter options.

The balanced parameter custom measurement provides the list of S parameter options. The network analyzer takes the menus provided by custom pieces and tacks them onto the Trace|Custom menu so that they are available to the user when the user is interacting with a custom measurement. The menu fragments are customized to the mixed mode measurement as they allow switching between them (SSS, SSD, SSC, etc.). When a standard measurement is active, the Trace|Custom menu pick is not available and not shown as a menu option.

Data post-processing is the process of mathematically manipulating raw acquired data, such as S-Parameters, arbitrary receiver ratios, or raw receiver data to produce a result suitable for displaying or downloading from an instrument. To produce data results, a set of mathematical algorithms is systematically applied to the raw data. After this is done, the desired set of data exists and is ready for export through a network, or for display on an analyzer's front panel.

As discussed above, in the preferred embodiment of the present invention, multiple parallel data post-processing chains exist side by side, which provides the ability to display multiple different data analyses side-by-side or overlaid on a display for comparison. In the preferred embodiment, each data processing chains is implemented as an instance of a software object, namely a Measurement.

A Measurement represents a unit data post processing. The job of the Measurement is to transform "raw" unprocessed measured data in the form of S-Parameters, arbitrary receiver ratios, or unratioed receiver data (hereafter referred to as "raw data") and produce one or more analysis results of that raw data. To do this job, the Measurement specifies all of the algorithms that will be used to process raw data and the order in which those algorithms are applied to the data to get the desired result data. The Measurement also provides services such as procuring raw data buffer inputs for the algorithms, managing intermediate data buffer results, and managing the final result data buffers.

The "Standard Measurement" is a measurement that is included as core software within an analyzer, and defines a 'standard' network analyzer result (basically, and S-Parameter, arbitrary receiver ratio, or raw receiver power measurement).

A "Custom Measurement" is a measurement that is written separate from the core software. For example, it is written by the analyzer manufacturer, a customer, or a third party. The custom measurement is compiled as a library that can be loaded and used to define data processing behavior.

An Algorithm (with a capital 'A') is a distinct data processing operation. An Algorithm is a function that takes as input some number of data buffers and coefficients, and produces some number of output data. In practice, the Algorithm is implemented as an object that contains state which performs the function of input coefficients, and which is invoked with a reference to a buffer store. The Algorithm draws input buffers from buffer storage and returns output buffers to buffer storage after computing results.

A series of Algorithms objects can be executed in sequence to produce one or more final results of interest to the network analyzer user. The user sets the coefficients on each of the algorithms via the Network Analyzer's user interface (UI). The input for a particular algorithm comes from either the hardware (i.e. raw data) or from the output of a previously executed Algorithm.

A "Standard Algorithm" is algorithm code that is included as part of the core software included in a 'standard' software package with the analyzer. This data processing code is used by the Standard Measurement to produce a result. Examples include Error Correction, Gating, Phase Correction, Formatting, Smoothing, Trace Math, Markers, and Limit Lines.

A "Custom Algorithm" is algorithm code that, like a Custom Measurement, is separate from the core software. It is written, for example, by a customer or third party. It is also packaged as a separate library that can be loaded by the analyzer if a measurement (of any type) calls for it to be used as part of data processing for that measurement.

In general, many different interesting results can be obtained by applying different Algorithms and Algorithm sequences to raw input data. A typical network analyzer measurement result is an S-Parameter. The raw input data is that same S-Parameter (a simple ratio of sampled data from two of the Network Analyzer's hardware receivers), so the algorithms employed by the measurement need only change the data to correct for errors or alter the format. Markers and limit testing can also be applied. A less typical measurement result is (for example) K-Factor. This measurement requires multiple S-Parameters as raw input data, and the K-Factor result is produced by way of a mathematical algorithm. K-Factor provides a figure of merit for an amplifier that may be more suitable than an S-Parameter.

In the preferred embodiment of the present invention, a "custom" software library is loaded that can define custom Measurements and/or custom Algorithms. This removes the need to retrieve network analyzer data and avoids the I/O time penalty that occurs when this processing is done outside the analyzer. In addition, the library writer can choose to use some of the standard or predefined data processing operations (Algorithms) to produce a final result. This means that for a custom result, analysis features like markers and limit lines need not be rewritten by the author of the custom computation code.

For example, a custom Measurement is written that specifies which raw S-Parameters are to be acquired by the hardware, specifies an Algorithm to be executed that will compute the K-Factor using those S-Parameters, and then specifies that the standard marker and limit line algorithms are applied to the K-Factor result data for more analysis of that result. This ability to write custom measurements and algorithms to augment the standard data processing operations produces a very integrated look and feel to a custom Measurement.

The data processing and user interface are integrated into the standard analyzer software framework, resulting in faster custom data processing with less programming effort, and the need for an external program or computer to perform the custom computation or network analyzer control operations is removed. This feature is more than just a program that can be loaded and executed on the analyzer to control data taking operation. This feature allows the program writer to customize the internal data processing of the analyzer software to produce data with the desired qualities.

As mentioned above, the Measurement is the basic unit of data post-processing in the analyzer. Each Measurement object employs one or more Algorithm objects to process data generated by the analyzer's hardware. The results are displayed on analyzer's display. The Measurement and Algorithm objects work together to turn raw data into the desired result.

Figure 8:
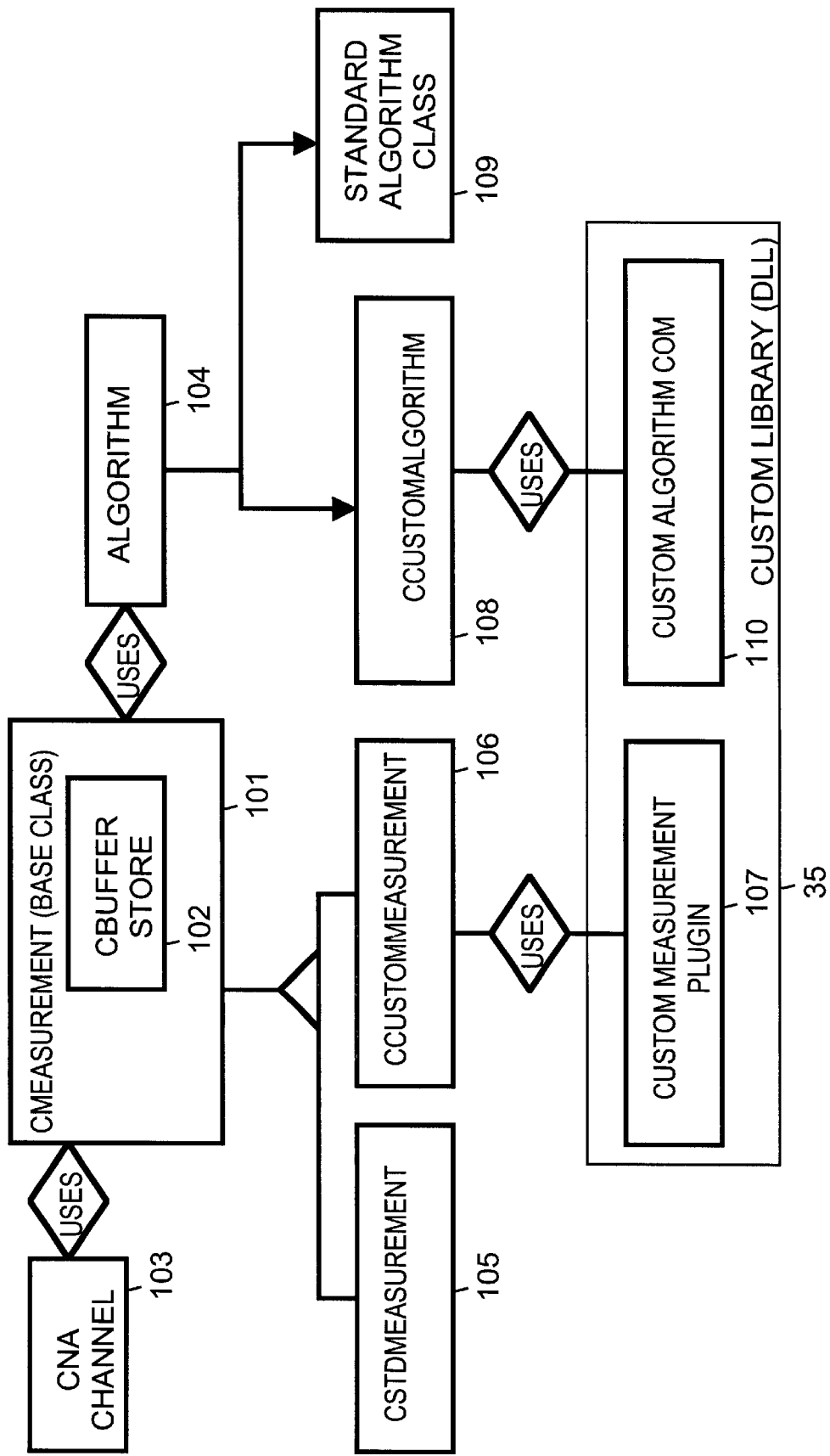
FIG. 8 is a chain entity relationship diagram in accordance with a preferred embodiment of the present invention.

FIG. 8 is an Entity Relationship Diagram for the preferred embodiment. CMeasurement class 101 is implemented as a C++ base class (sometimes referred to as the measurement framework). This base class provides much of the functionality required for setting up and processing data. The standard and custom measurements are implemented as derived classes of Measurement (CStdMeasurement 105, and CCustomMeasurement 106, respectively). They provide specific implementations of the more general Measurement behavior where necessary. For example, when creating a new custom measurement, CCustomMeasurement 106 takes care of loading the custom library code and creating the custom measurement plugin object, whereas CStdMeasurement 105 has the standard functionality built in at the factory and doesn't need to do this.

Also, the Measurement maintains a store of data buffers as a service to the Algorithm objects that it will execute. This is the "global" store represented in FIG. 8 by CBufferStore 102. The CMeasurement can also manage more than one list of Algorithms to execute. This permits the same Algorithms (that were created by the Measurement) to be executed more than once against different data buffer stores, to produce the same or a similar analysis of different data. The object that is used by the Measurement to keep the list of Algorithms and maintain a buffer store is called a DataPath.

CMeasurement 101 is a base class to CCustomMeasurement 106 and CStdMeasurement 105. CMeasurement 101 provides implementation common to both types of measurements, such as CBufferStore 102 and requesting raw buffers from the acquisition subsystem.

CStdMeasurement 105 has a factory fixed set of Algorithms to use to compute S-Parameters. CCustomMeasurement 106 loads a custom library containing a custom measurement plugin that defines a list of Algorithms (possibly including custom Algorithms) to be used to produce the measurement's result.

As shown in FIG. 8, Algorithm 104 is a base class to CCustomAlgorithm 108 and Standard Algorithm Class 109.

Within a custom library (DLL) 35 reside a custom measurement plugin 107 and a custom algorithm 110. The information within custom library 35 are defined by individual users. All the other code outside custom library 35 shown in FIG. 8 comes as part of the software included with the analyzer.

Figure 9:
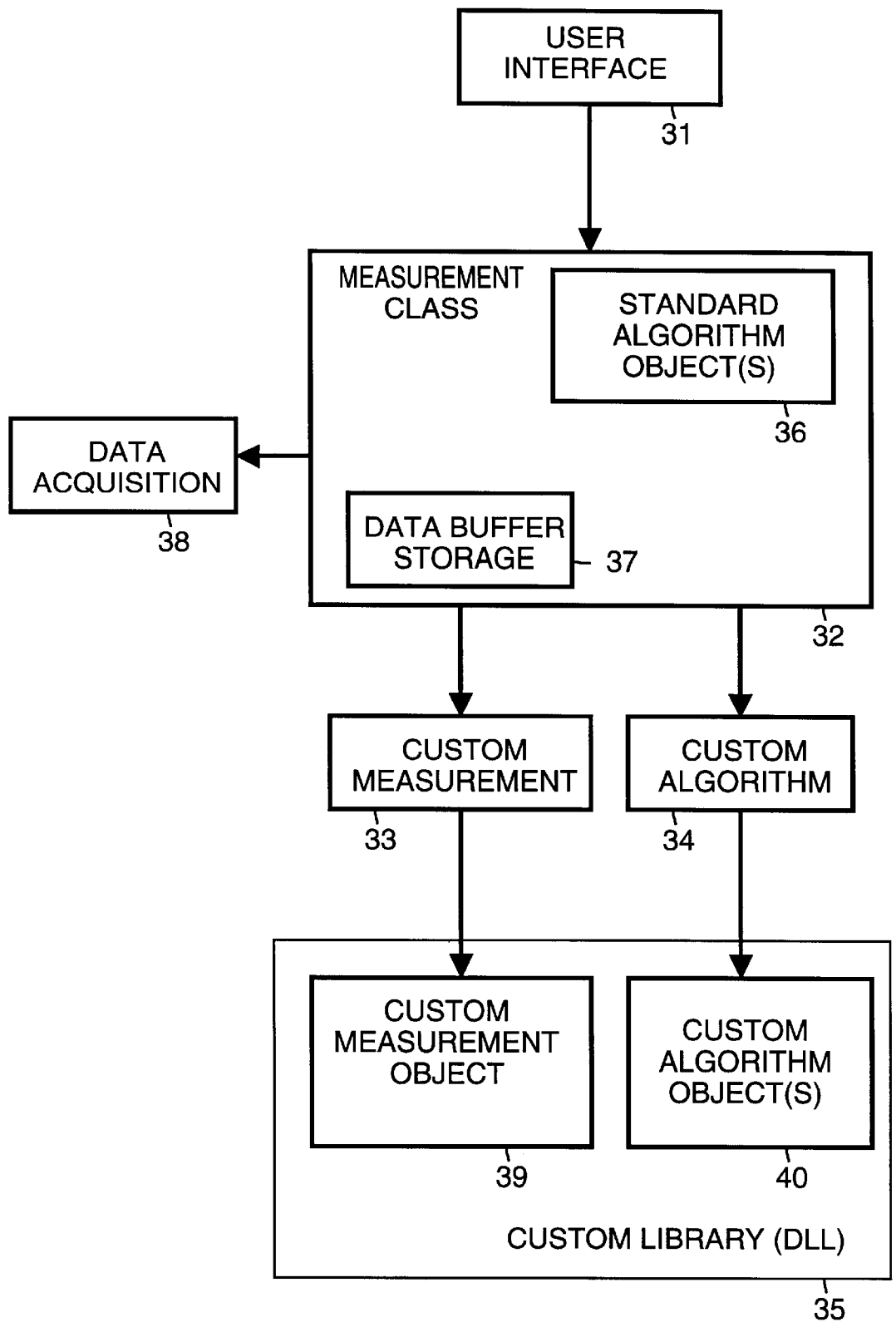
FIG. 9 illustrates control flow during measurement creation (setup) in accordance with a preferred embodiment of the present invention.

FIG. 9 illustrates set-up of a new Measurement. The process is started when the user wishes to create a new Measurement. The analyzer distinguishes between two different measurement types, Standard and Custom. If the user chooses to create a Standard Measurement, then a CStdMeasurement object is created. This is code that is included with the analyzer as core software. If the user chooses a Custom Measurement, then a CCustomMeasurement object is created, which in turn loads the custom library containing the requested custom Measurement plugin. Then that custom measurement plugin object is created. Custom Measurement plugins make themselves known to the analyzer software by registering a Microsoft Component Object Module (COM) component category when the Custom Measurement plugins are installed on the analyzer. The actual loading of the library and creation of the custom COM Measurement object is taken care of by the COM infrastructure because the custom measurement object is a COM object. In either case, the analyzer has a Measurement object that is ready to use.

The Measurement is then queried for the list of algorithms that it will employ to do its data processing for the primary data processing "path" (or DataPath). This list is in the form of GUIDs (Globally Unique Identifiers) that refer either to the CLSID (Class ID) of a custom Algorithm (a COM object) or a predefined ID of a standard Algorithm provided by analyzer. The analyzer creates one Algorithm object corresponding to each GUID in the list, and stores those Algorithm objects in a list. The analyzer then queries each Algorithm for its input buffer data requirements. In the preferred embodiment, buffer requests fall into three basic categories.

The first category is the output of previous Algorithms. This means that an Algorithm doesn't really care what its input data is. The Algorithm takes as its input whatever the previous Algorithm in the sequence outputs.

The second category is a specific named buffer. This means that when the Algorithm processes data it will request a specific buffer from the Measurement's store of buffers.

The third category is a buffer containing a specific type of data. This means that an Algorithm can request S-Parameter, arbitrary ratio, or raw receiver results. These buffers don't necessarily contain raw data, but may contain data of the requested type that has been processed by previous Algorithms (but still retains its type).

From the aggregate list of inputs analyzer determines what raw data must be acquired from the Network Analyzer hardware, and puts in a request for those data to the acquisition subsystem. The acquisition subsystem will notify the Measurement when data corresponding to those requests becomes available.

The Measurement is then queried for a label and some other miscellaneous information is used to construct annotation and menu commands (in the custom Measurement case).

FIG. 9 illustrates the above-described set-up process. A user uses user interface 31 to instruct measurement class 32 to select a custom measurement 33 to load or create. Custom measurement 33 loads the appropriate custom library (DLL) 35 and creates custom measurement object 39 using standard COM techniques. Custom measurement object 39 is queried for the list of Algorithms it wishes to employ in order to produce its final results. This is a list of GUIDs that identifies custom algorithm objects 40 and/or standard algorithm objects 36. Custom algorithm 34 is used to create custom algorithm object(s) 40 within the system. Measurement class 32 queries each algorithm object for its data requirements. Any data requests that are for "Raw" acquisition data are forwarded to data acquisition subsystem 38. Other data is produced, for example, by algorithms. Once set-up has been performed, data acquisition subsystem 38 notifies the measurement framework when data input is acquired. Data buffer storage 37 is used to store data.

Once the Measurement has completed the setup phase, it is ready to participate in processing data that is acquired by data acquisition subsystem 38.

Figure 10:
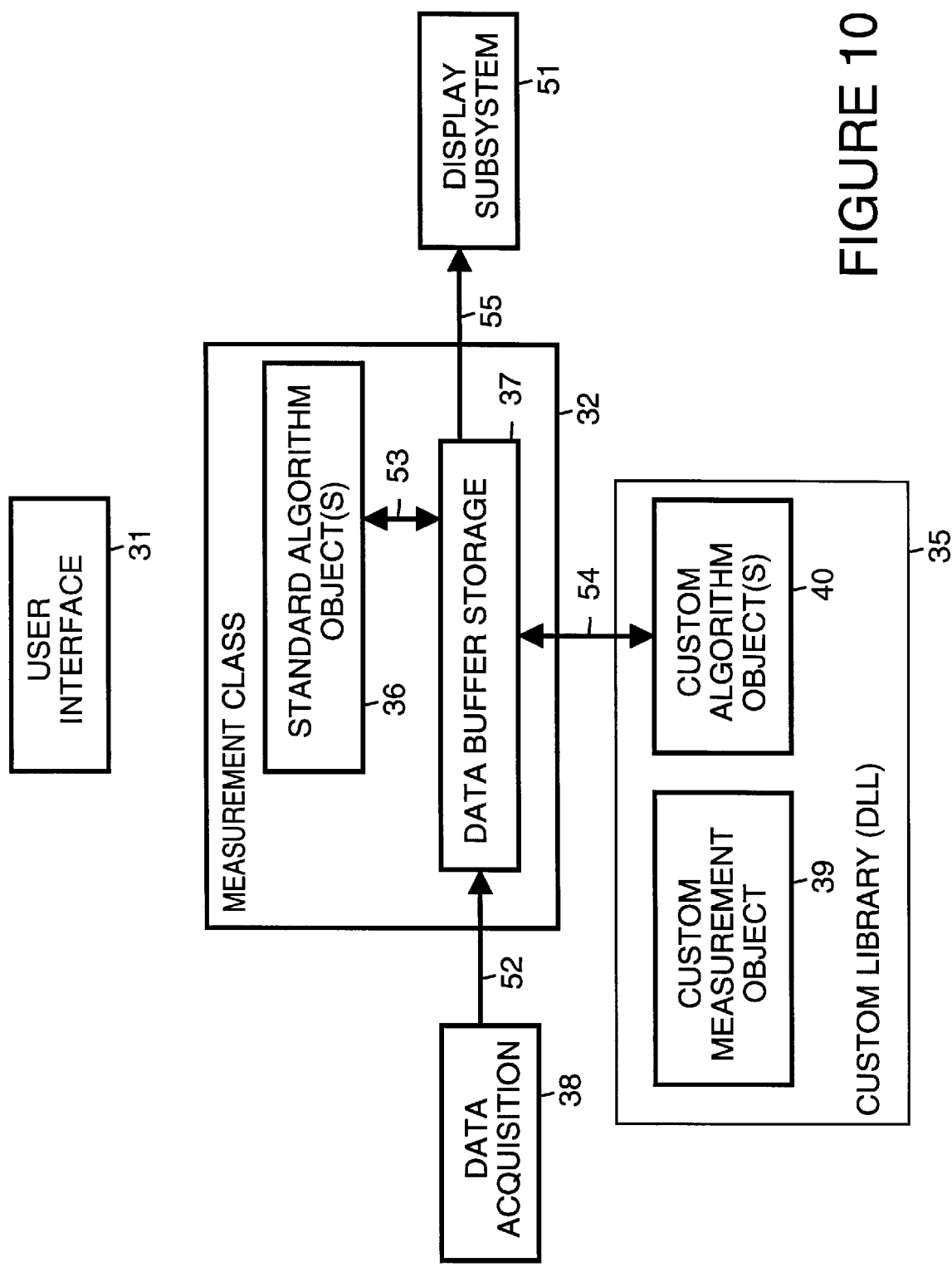
FIG. 10 illustrates data processing sequence in accordance with a preferred embodiment of the present invention.

FIG. 10 illustrates the data processing sequence. Data is acquired by data acquisition subsystem 38. That data is transferred to data buffer storage 37. Data is processed by various algorithms (either Custom or Standard) in an order specified by custom measurement object 39. Data processing for an algorithm (either standard algorithm object 36 or custom algorithm object 40) includes retrieving 0 or more 'input' data buffers from data buffer storage 37, computing a result using those input buffers and any settings in the Algorithm object itself, and then storing 0 or more 'output' data buffers back into the data buffer storage 37. Custom Algorithms objects 40 use the IBufferStore interface during this stage to retrieve and replace data buffers. Standard Algorithms objects 36 use an internal mechanism for buffer transfer.

Then, several final result buffers, including those holding trace data, marker data, limit line data, etc. are transferred to Display Subsystem 51 where the data is turned into graphical representations.

The order in which Algorithms are processed is significant, as it affects what data are available to any particular Algorithm at any point in time. When processing the data, Custom Algorithms are treated very similarly to the Standard Algorithms, making the custom data processing transparent to the user of the instrument.

When the raw data requested by the Measurement becomes available from data acquisition subsystem 38, the Measurement will 'execute' a Measurement Result (MR) Chain. An MR chain encapsulates both an Algorithm and result data for the Algorithm. The basic process is to execute a specific function, "ProcessData", on each Algorithm object in the order the Algorithms were originally specified. After this, the analyzer notifies other subsystems (such as the Display) of changed Algorithm result data, which is retrieved (and in the case of the Display, drawn on the screen). The Measurement object that is executing the Algorithms does not differentiate between standard or custom Algorithms since their behavior is identical from its point of view.

Each Algorithm implements the ProcessData method. During this method (function) call, each Algorithm performs three basic operations. The first operation is to retrieve (input) data from the provided data store. The second operation is to compute result data. The third operation is to put the result (output) data back into the provided data store.

So, Algorithms take input buffers and produce output buffers. These data buffers are contained in a data store (buffer storage) ultimately maintained by the Measurement (there can be more than one). Data buffers in this store are accessible to Algorithms during the ProcessData function.

Each algorithm uses various inputs, such as raw data or output data from a previous algorithm, along with its settings to produce its own output data. Typical Algorithms used to process the data include user error correction, phase correction, time domain transform, formatting, markers, and limit lines.

Buffers are stored, maintained, and recalled by the system. To accommodate custom measurements and algorithms, it is necessary to have a buffer namespace processing that is expandable. A simple enumeration system would not be sufficient. In the preferred embodiment, the analyzer uses a text based buffer naming scheme to provide this expandable namespace. Each data buffer in the system has a text name and is stored in a map under that name. As discussed above, there are three categories of Algorithm input requirements. Having named buffer supports the type where specific named buffers are supported.

When buffers are output from previous algorithm or when the buffer contains a specific type of data, these buffers are accommodated by buffer name aliases. In the preferred embodiment, a set of aliases are defined so that buffers maintained by the Measurement can be referred to in an abstract fashion. For example, if an Algorithm required as input whatever the previously executing Algorithm had as output, then it would request the buffer "PreviousOutput". The framework can take into account the Algorithm's position in the execution chain, and determine the meaning of "PreviousOutput" for that buffer. This satisfies the case where buffers are output of previous algorithm, and is the key to allowing a large class of Algorithms (those that are more or less order independent) to be arranged in an arbitrary order and successfully executed.

When the Algorithm requires a buffer to have a specific type of data, another buffer name aliasing scheme (working in parallel to the first aliasing) is in place. In this scheme, the buffer can request (for example) "S11" (a text string), and the framework determines which buffer was the last one produced that contains $S_{11}$ data, and returns that to the requesting Algorithm. This technique allows algorithms that require data with a specific type or character to be properly obtained from the data store even when paired with Algorithms of unknown type or when executed in a different order.

For example, to produce the sum of $S_{11}$ and $S_{21}$ as the final result, and to have this algorithm work with the standard error correction algorithm, buffer content aliasing scheme is used. In this simple example, a custom measurement would set up its Algorithm list to have the standard error correction first, followed by a custom S-Parameter adder second. This way, the custom S-Parameter sum algorithm would request and get $S_{11}$ and $S_{21}$ data regardless of whether error correction for those S-Parameters was being applied. If the error correction algorithm is on and producing error corrected versions of $S_{11}$ and $S_{21}$, then the summing algorithm would get those error corrected versions when requesting "S11" and "S21". If the error correction algorithm is off and not correcting the S-Parameters, then the measurement framework would deliver raw, uncorrected versions of $S_{11}$ and $S_{21}$ from the acquisition subsystem. As a third possibility, the S-Parameter adder Algorithm could request "RawS11" and "RawS21" to retrieve (by name and not by alias) the raw versions of those data regardless of whether error correction was in operation.

In order for custom Measurement objects (which are COM objects) to interact with the analyzer framework code, in the preferred embodiment, the measurement objects support a pre-defined interface that allows the analyzer framework to control the custom Measurement and get information from it. The pre-defined interface is, for example, ICustomMeasurementPlugin, and its Interface Definition Language (IDL) description is set out in Table 3 below:

TABLE 3

```
[
    object,
    uuid(4E14D53C-CA1D-11d4-AD48-00108334AE98),
    helpstring("ICustomMeasurementPlugin
        Interface"),
    pointer_default(unique)
]
// This interface is prototype and subject to
        change before product shipment!
interface ICustomMeasurementPlugin : IUnknown
{
    HRESULT Initialize ( [in] ICustomMeasurement *
        pMeas );
    [propget] HRESULT Label ( BSTR * pLabel );
    HRESULT Setup( [in] HWND hWnd, [in] IUnknown *
        pInitializer, [in] short bGUI );
    [propget] HRESULT Name([out , retval] BSTR
        *pVal);
    HRESULT GetAlgorithmList( [in,out] long
        *pListLength, [out,
    size_is(*pListLength)] GUID *Vals );
    HRESULT GetCustomMenu( [out] HMENU *pMenu );
    HRESULT OnMenuPick( [in] HWND hParentWnd, [in]
        unsigned long pickVal );
};
```

A Custom Measurement is actually a pair of software pieces. There is a "Custom Measurement Plugin", which is the COM object written by the custom measurement writer. The "Custom Measurement" is the analyzer framework code that takes care of loading, using, and providing services to the Custom Measurement Plugin on behalf of the analyzer framework software.

As can be seen in the ICustomMeasurementPlugin interface, there are several methods, which are summarized in Table 4 below:

TABLE 4

— Initialize - Called after the custom measurement plugin is created, provides the plugin with a pointer back to the analyzer which it can use to get information from the analyzer.
— Label property. Provides analyzer with a text label for the plugin.
— Setup. Called after Initialize and GetAlgorithmList, after Algorithms have been created. Provides the plugin with the opportunity to set up Algorithms or present a custom UI to the user.
— Name property. Provides analyzer with a text name for the plugin.
— GetAlgorithmList. Must return a list of GUIDs referring to Algorithm objects to be created and used for this Measurement.
— GetCustomMenu. Must return 0, or a menu handle to a Windows menu fragment. This allows the plugin to provide a menu UI that the analyzer framework will integrate into the menu structure of the application when this custom measurement is in use.
— OnMenuPick - Called when the user selects a menu pick on the plugin's menu fragment. The plugin is provided with the ID of the menu pick so that it can take the appropriate action.

All of the ICustomMeasurementPlugin interface methods are used during the setup phase of the Measurement with the exception of OnMenuPick, which is called whenever the user selects a pick from the custom menu fragment.

Like the custom measurement plugin which supports the ICustomMeasurementPlugin interface, any custom Algorithms that are written supports an interface tailored to them in order to be used by analyzer. This interface is the IAlgorithm interface, as set out in Table 5 below:

TABLE 5

```
[
    object,
    uuid(A7D46BF9-D523-11d4-AD48-00108334AE98),
    helpstring("IAlgorithm Interface"),
    pointer_default(unique)
]
// This interface is prototype and subject to change before
        product shipment!
interface IAlgorithm : IUnknown
{
    [propget] HRESULT Name([out, retval] BSTR *pVal);
    HRESULT SetupDataRequests(
            [in,out] long *pListLength,
            [in, size_is(*pListLength)] BSTR
    Current Vals[],
            [in,out] long *pNewListLength,
            [out, size_is(*pNewListLength)] BSTR
    NewVals[],
            [in,out] long *pRemoveListLength,
            [out, size_is(*pRemoveListLength)] BSTR
    RemoveVals[]
            );
    HRESULT GetDataOutputs(
            [in,out] long *pListLength,
            [out, size_is(*pListLength)] BSTR Vals[],
            [out, size_is(*pListLength)]
    OUTPUT_DATA_TYPE Types[]
            );
```

TABLE 5-continued

```
    HRESULT ProcessData( [in] DATAPROCESS_TYPE
        processType, [in] short bNewSweep, [in]
    IBufferStore* pBufStore);
    HRESULT Initialize( [in] IUnknown* pMeasurement );
        HRESULT GetCustomMenu( [out] HMENU *pMenu );
        HRESULT OnMenuPick( [in] HWND hParentWnd, [in]
            unsigned long pickVal );
};
```

The methods on this interface are summarized in Table 6 below:

TABLE 6

— Name property. Should return the string name of the Algorithm.
— SetupDataRequests. The analyzer framework calls this method to determine what data buffers are required by this Algorithm. The Algorithm should set return values appropriate to its requirements.
— GetDataOutputs. The analyzer framework calls this method to determine what data buffers are produced by this Algorithm. The framework uses this information to allocate space for this output data so that it will be available during a subsequent call to ProcessData.
— ProcessData. This is the most important method. The analyzer framework calls this method when it wants this Algorithm to process some data. Information about how the data is to be processed, as well as a pointer to a buffer store interface where data buffers can be found and deposited are provided. This is where the Algorithm gets work done.
— Initialize. Similar to ICustomMeasurementPlugin::Initailize. The framework calls this at Algorithm creation time and provides the Algorithm with a pointer back to the measurement so that it can be referenced later by the Algorithm.
— GetCustomMenu. Similar to ICustomMeasurementPlugin::GetCustomMenu. Algorithms can provide custom menu fragments so that they can be controlled by the analyzer. The analyzer framework calls this method shortly after creating the Algorithm.
— OnMenuPick. Similar to ICustomMeasurementPlugin::OnMenuPick. The analyzer framework calls this method when the user selects a menu pick from the Algorithm's menu fragment.

In addition to the ICustomMeasurementPlugin and IAlgorithm interfaces which are implemented by the custom code, there are interfaces defined through which the custom code (measurements and algorithms) can access the analyzer. One of these is the IBufferStore interface, as set out in Table 7 below:

TABLE 7

```
///////////////////////////////////////////////////////////////
// IBufferStore interface
// Intended to be supported by Datapath wrapper. This will
// allow custom algorithms
// access to the buffers they require to do their work.
///////////////////////////////////////////////////////////////
[
    object,
    uuid(9983AA69-13F9-11d5-AD4C-00108334AE98),
    helpstring("IBufferStore Interface"),
    pointer_default(unique)
]
interface IBufferStore : IUnknown
{
    [helpstring("method GetBuffer")]
        HRESULT GetBuffer(
            [in] BSTR bufName,
            [in,out] long * pLengthBytes,
```

TABLE 7-continued

```
            [out] BUFDATA_TYPE* pBufType,
            [out] long * plValidIndex,
            [out,size_is(,*pLengthBytes)]
                unsigned char **pVal
            );
    [helpstring("method GetBuffer2")]
        HRESULT GetBuffer2(
            [in] BSTR bufName,
            [out,retval] IDataBuffer ** ppBuf
        );
    [helpstring("method GetTypedBuffer")]
        HRESULT GetTypedBuffer(
            [in] BSTR bufName,
            [in] BUFDATA_TYPE type,
            [out,retval] IDataBuffer ** ppBuf
        );
    [helpstring("method GetInputBuffer")]
        HRESULT GetInputBuffer(
            [in] GUID AlgID,
            [in] BSTR bufName,
            [in,out] long * pLengthBytes,
            [out] BUFDATA_TYPE* pBufType,
            [out] long * plValidIndex,
            [out,size_is(,*pLengthBytes)]
                unsigned char **pVal
        );
    [helpstring("method GetInputBuffer2")]
        HRESULT GetInputBuffer2(
            [in] GUID AlgID,
            [in] BSTR bufName,
            [out,retval] IDataBuffer ** ppBuf
        );
    [helpstring("method GetLastSParamInputBuffer")]
        HRESULT GetLastSParamInputBuffer(
            [in] GUID AlgID,
            [in] long lRcvPort,
            [in] long lSrcPort,
            [out,retval] IDataBuffer ** ppBuf
        );
    [helpstring("method PutOutputBuffer")]
        HRESULT PutOutputBuffer(
            [in] BSTR bufName,
            [in] long lLengthBytes,
            [in] BUFDATA_TYPE BufType,
            [in] long lValidIndex,
            [in, size_is(lLengthBytes)] unsigned
                char *pVal
        );
    [helpstring("method CopyBufferStimulusInfo")]
        HRESULT CopyBufferStimulusInfo(
            [in] BSTR srcBufName,
            [in] BSTR destBufName
        );
};
```

The IBufferStore interface is supported by the measurement framework, and exists so that custom Algorithms can get data from and return to the measurement's data store when their ProcessData method is called. Alternatively, other interfaces may be used instead of IBufferStore. The GetInputBuffer2 method takes as input a string (BSTR) as input, and returns an IDataBuffer interface which provides access to data in the requested buffer. As can be seen by this interface, buffers are addressed by string names.

In the preferred embodiment of the present invention there are several key elements. The first key element is polymorphic behavior for Measurements and Algorithms. Polymorphic behavior means that different objects can implement the "same" functionality in a different way, so that the user of that object is isolated from any differences. In this design, both Measurement and Algorithm objects are abstractions, with different concrete implementations underneath that handle the standard and custom variants of each. This allows the data processing framework code to function the same while the differences between the standard and custom measurements are handled within that code. Polymorphism is a standard concept, but it is being used in this instance to smoothly integrate an externally generated custom measurement into the analyzer's data processing.

The second key element is partitioning of Measurement and Algorithm functionality. By assigning specific behaviors to Measurement and Algorithm objects, this system is able to isolate the requirements for them and therefore cleanly support other (i.e. custom) implementations. The Measurement's core responsibility is to provide a list of Algorithms which are to be executed by the framework. The Algorithm's core responsibility is to complete one step in a larger data processing 'chain'. These partitions allow the partitioned items to be swapped in and out and still work together.

The third key element is the Measurement Framework provides most of the data processing functionality. The Measurement Framework ("Framework"), which works polymorphically with either standard or custom measurements and standard or custom algorithms provides much of the functionality required for the data processing. The framework takes care of loading and unloading measurements. It takes care of managing data buffers for the measurement and algorithms. It takes care of executing the Algorithms (with the exception of the ProcessData method, which is implemented by each Algorithm), in particular when to execute them (such as when new data is acquired or when algorithm state changes, or other times). All of these tasks are provided and available to both the standard and custom measurement types. In particular, because all of this work is separated from the custom measurement plugin and custom algorithms, this makes writing these custom pieces out in the field much easier than it otherwise would be.

The fourth key element is that Algorithms are separate from data. This is somewhat related to the last point. From the point of view of the last point, this is good because it simplifies the implementation of an Algorithm object to have another object provide data buffer management services. This is also important because it allows the framework to apply an algorithm to different data sets.

The fifth key element is that buffers are stored using an expandable namespace, and have aliases. By using a namespace that is expandable, namely text strings, custom code can add data buffers to the system as necessary. Providing a general buffer name aliasing system allows any Algorithm to refer to buffers not produced by it by referring to the qualities of the buffers. This allows Algorithms that were written at different times or places to be able to work with the measurement framework and with one another.

An additional key element is modifying the data processing to produce a different Measurement Result—outside the factory. After the analyzer leaves the factory, custom libraries can be added to it that can alter the data processing, which effectively allows different measurement results to be obtained (such as K-Factor, Y-Parameters, etc) while still maintaining an integrated look and high speed. The factory shipped code makes only limited assumptions about what the result of a custom measurement is, specifically that the data produced is in a particular format (including arrays (for trace and limit line data), and marker data structure), which allows more flexibility as to what can be implemented in custom measurements and algorithms.

An additional key element is that custom Algorithms and custom Measurements can provide their own GUI. In order to be able to properly control a measurement or algorithm that was loaded into analyzer after it left the factory, that custom component provides a GUI control mechanism to control the specifics of that custom piece of code. The analyzer accommodates that control mechanism in a general fashion so that various user interfaces specific to the custom code can be supported.

An additional key element is that custom Algorithms and custom Measurements are programmable. In the preferred embodiment, Automation (COM) model is used to program the custom components. Automation (COM) or SCPI (over GPIB or LAN) interface can be used to control all of the standards aspects of the software. In general, the utility of the analyzer is enhanced by being able to control it programmatically. Custom measurements and custom Algorithms are exposed through the Automation model so that they can be programmed just as the rest of the standard measurements and other network analyzer code can be. This allows creation and manipulation of custom algorithms and measurement from the GUI, and also allows this to be done programmatically.

In alternate embodiments of the present invention, the same sort of customization capability is implemented for the display subsystem. This allows custom display widgets to be written and loaded by the analyzer to provide display capabilities that were not available when the instrument was shipped from the factory. This would be useful in the case where, for example, a custom measurement was written the produced data that was in a non-standard format for whatever reason. Currently the analyzer display can only draw data traces, limit lines, markers, and some annotation. But when the analyzer's display employs the same techniques as the measurement framework described herein, the display can load a custom display widget to handle the non-standard (custom) data and display it properly.

The foregoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

I claim:

1. An electronic instrument comprising:
   instrument hardware for acquiring unprocessed measured data;
   core software, the core software including:
      standard measurement objects that produce analysis results of the unprocessed measured data, and
      standard algorithms that are used by the standard measurement objects to aid in production of analysis results of the unprocessed measured data; and,
   a custom library, separate from the core software, the custom library including:
      custom measurement objects that produce analysis results of the unprocessed measured data, and
      custom algorithms that are used by the custom measurement objects to aid in production of analysis results of the unprocessed measured data;
   wherein the custom measurement objects also are capable of using the standard algorithms to aid in production of analysis results of the unprocessed measured data.

2. An electronic instrument as in claim 1 wherein each custom measurement object includes a list of algorithms to be executed.

3. An electronic instrument as in claim 1:
   wherein the electronic instrument additionally comprises a display; and,
   wherein the custom measurement objects each present a graphic user interface on the display to a user.

4. An electronic instrument as in claim 1:
   wherein the electronic instrument additionally comprises a display;
   wherein the core software presents a graphic user interface on the display to a user; and,
   wherein the custom measurement objects also each present a graphic user interface on the display to a user, the graphic user interface presented by the custom measurement objects being integrated with the graphic user interface presented by the core software.

5. An electronic instrument as in claim 1 wherein the core software loads and unloads the custom measurement objects.

6. An electronic instrument as in claim 1 wherein the core software includes implementation of buffer storage, the buffer storage storing buffers used by the standard algorithms and the custom algorithms.

7. An electronic instrument as in claim 1 wherein the core software includes implementation of buffer storage, the buffer storage storing buffers used by the standard algorithms and the custom algorithms, wherein the standard algorithms and the custom algorithms retrieve data from input buffers and place data in output buffers.

8. An electronic instrument as in claim 1 wherein the electronic instrument is a network analyzer.

9. A method performed by an electronic instrument that includes instrument hardware that acquires unprocessed measured data, the method comprising the following steps:
   (a) implementing standard measurement objects and standard algorithms using core software of the electronic instrument, the standard measurement objects producing analysis results of the unprocessed measured data, the standard algorithms being used by the standard measurement objects to aid in production of analysis results of the unprocessed measured data; and,
   (b) implementing custom measurement objects and custom algorithms using a custom library, separate from the core software, the custom measurement objects producing analysis results of the unprocessed measured data, and the custom algorithms being used by the custom measurement objects to aid in production of analysis results of the unprocessed measured data, wherein the custom measurement objects also are capable of using the standard algorithms to aid in production of analysis results of the unprocessed measured data.

10. A method as in claim 9 wherein in step (b) each custom measurement object includes a list of algorithms to be executed.

11. A method as in claim 9 additionally comprising the following step:
   (c) providing a graphic user interface on a display of the electronic instrument, including the following substep:
      (c.1) presenting a custom graphic user interface segment on the 6 display to a user.

12. A method as in claim 9 wherein step (b) includes the following substep:
   (b.1) loading and unloading the custom measurement objects by the core software.

13. A method as in claim 9 additionally comprising the following step:
   (c) implementing buffer storage by the core software, including the following substep:
      (c.1) storing buffers used by the standard algorithms and the custom algorithms.

14. A method as in claim 9 additionally comprising the following step:

(c) implementing buffer storage by the core software, including the following substeps:
(c.1) storing buffers used by the standard algorithms and the custom algorithms,
(c.2) retrieving, by the standard algorithms and the custom algorithms, data from input buffers, and
(c.3) placing, by the standard algorithms and the custom algorithms, data in output buffers.

15. Storage media for storing software, the software, when executed on an electronic instrument that includes instrument hardware that acquires unprocessed measured data, performing a method comprising the following steps:
(a) implementing standard measurement objects and standard algorithms using core software of the electronic instrument, the standard measurement objects producing analysis results of the unprocessed measured data, the standard algorithms being used by the standard measurement objects to aid in production of analysis results of the unprocessed measured data; and,
(b) implementing custom measurement objects and custom algorithms using a custom library, separate from the core software, the custom measurement objects producing analysis results of the unprocessed measured data, and the custom algorithms being used by the custom measurement objects to aid in production of analysis results of the unprocessed measured data, wherein the custom measurement objects also are capable of using the standard algorithms to aid in production of analysis results of the unprocessed measured data.

16. Storage media as in claim 15 wherein in step (b) each custom measurement object includes a list of algorithms to be executed.

17. Storage media as in claim 15 wherein the method additionally comprises the following step:
(c) providing a graphic user interface on a display of the electronic instrument, including the following substep:
(c.1) presenting a custom graphic user interface segment on the display to a user.

18. Storage media as in claim 15 wherein step (b) includes the following substep:
(b.1) loading and unloading the custom measurement objects by the core software.

19. Storage media as in claim 15 wherein the method additionally comprises the following step:
(c) implementing buffer storage by the core software, including the following substep:
(c.1) storing buffers used by the standard algorithms and the custom algorithms.

20. Storage media as in claim 15, wherein the method additionally comprises the following step:
(c) implementing buffer storage by the core software, including the following substeps:
(c.1) storing buffers used by the standard algorithms and the custom algorithms,
(c.2) retrieving, by the standard algorithms and the custom algorithms, data from input buffers, and
(c.3) placing, by the standard algorithms and the custom algorithms, data in output buffers.

21. An electronic instrument comprising:
instrument hardware for acquiring measured data;
core software, the core software including standard processing tools for processing the measured data; and,
a custom library interface that interfaces with custom libraries separate from the core software, each custom library including custom processing tools for processing the measured data, the custom processing tools being able to use the standard processing tools when processing the measured data.

22. A method performed by an electronic instrument that includes instrument hardware that acquires measured data, the method comprising the following steps:
(a) implementing, in core software of the electronic instrument, standard processing tools that processes the measured data; and,
(b) implementing a custom library interface that interfaces with custom libraries, separate from the core software, each custom library including custom processing tools for processing the measured data, the custom processing tools being able to use the standard processing tools when processing the measured data.

* * * * *